US00PP24716P3

(12) United States Plant Patent
Dibley

(10) Patent No.: US PP24,716 P3
(45) Date of Patent: Jul. 29, 2014

(54) ***STREPTOCARPUS* PLANT NAMED 'SLSDB17-0'**

(50) Latin Name: ***Streptocarpus* hybrid**
Varietal Denomination: SLSDB17-0

(71) Applicant: Lynne Dibley, Ruthin (GB)

(72) Inventor: Lynne Dibley, Ruthin (GB)

(73) Assignee: Dibleys Nursery (GB)

( * ) Notice: Subject to any disclaimer, the term of this patent is extended or adjusted under 35 U.S.C. 154(b) by 0 days.

(21) Appl. No.: 13/694,735

(22) Filed: Dec. 27, 2012

(65) Prior Publication Data

US 2014/0189917 P1 Jul. 3, 2014

(51) Int. Cl.
*A01H 5/00* (2006.01)

(52) U.S. Cl.
USPC ..... Plt./333

(58) Field of Classification Search
USPC ..... Plt./333
See application file for complete search history.

*Primary Examiner* — Anne Grunberg
(74) *Attorney, Agent, or Firm* — Cassandra Bright

(57) ABSTRACT

A new and distinct *Streptocarpus* cultivar named 'SLSDB17-0' is disclosed, characterized by large, unusually marked flowers with white upper lobes and heavily veined lower lobes. Plants are highly floriferous. The new variety is a *Streptocarpus*, suitable as an outdoor garden or container plant.

2 Drawing Sheets

Figure 1:
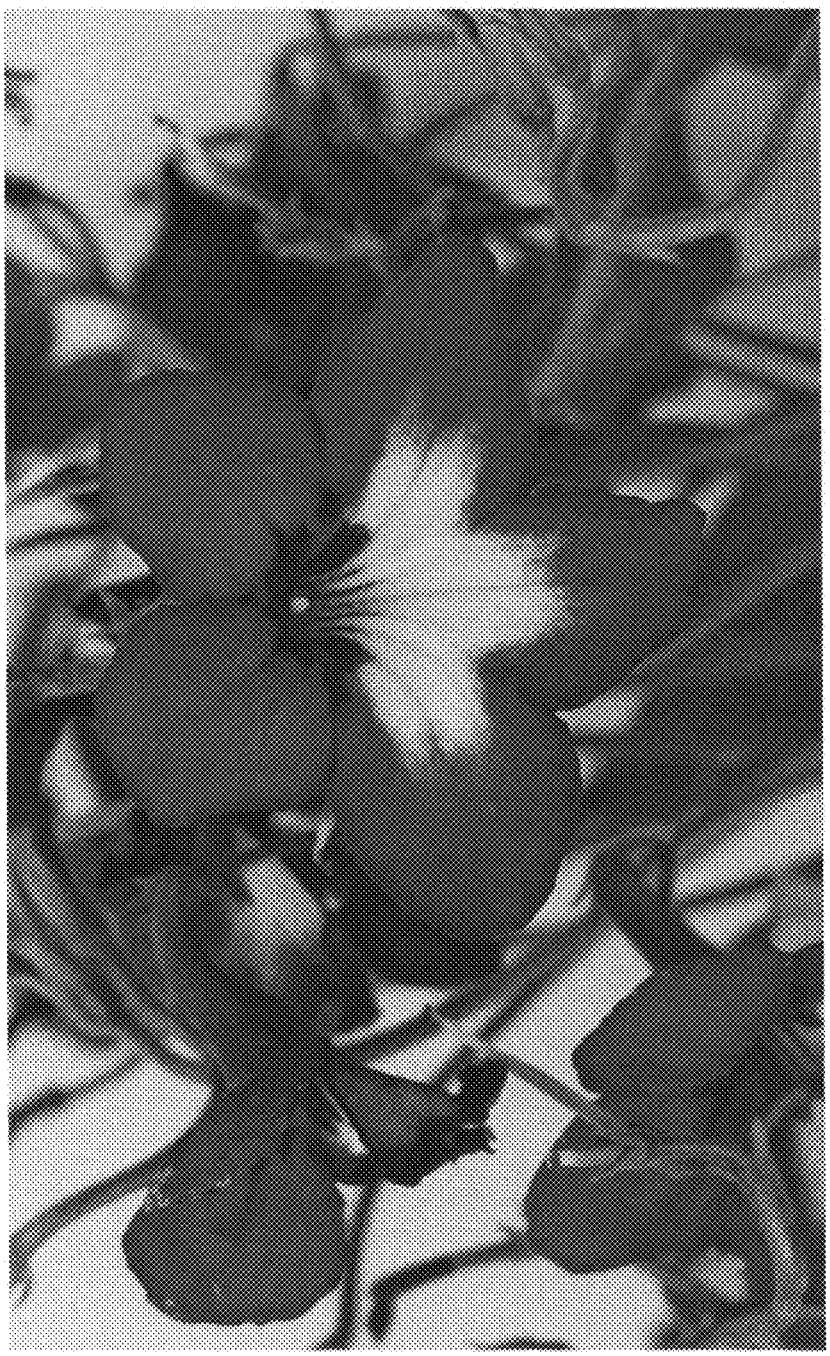

Latin name of the genus and species: *Streptocarpus* hybrid.
Variety denomination: 'SLSDB17-0'.

The new *Streptocarpus* cultivar is the product of a planned breeding program by the inventor Lynne Dibley, a citizen of United Kingdom. The breeding program was carried out at a commercial nursery in Ruthin, United Kingdom. The objective of the breeding program was to develop new *Streptocarpus* varieties with good characteristics for ornamental purposes.

The new variety resulted from the crossing of the seed parent, an unnamed, unpatented proprietary *Streptocarpus* seedling with the pollen parent, an unnamed, unpatented proprietary *Streptocarpus* seedling in 2010. The new variety was discovered in 2011 by the inventor in a group of seedlings resulting from the 2010 crossing, at a commercial nursery in Ruthin, United Kingdom.

Asexual reproduction of the new cultivar 'SLSDB17-0' by vegetative cuttings was first performed at a commercial greenhouse in Ruthin, United Kingdom in 2011. Subsequently at least three generations have been produced from vegetative cuttings, and have shown that the unique features of this cultivar are stable and reproduced true to type.

SUMMARY OF THE INVENTION

The cultivar 'SLSDB17-0' has not observed under all possible environmental conditions. The phenotype may vary somewhat with variations in environment such as temperature, day length and light intensity, without however, any variance in genotype.

The following traits have been repeatedly observed and are determined to be the unique characteristics of 'SLSDB17-0.' These characteristics in combination distinguish 'SLSDB17-0' as a new and distinct *Streptocarpus* cultivar:

1. Large flowers size.
2. Heavily veined on lower 3 floral lobes.
3. Highly floriferous plants.

4. White upper lobes.
5. Unusual flower markings.

COMPARISON TO THE PARENT VARIETIES

Plants of the new cultivar 'SLSDB17-0' are similar in most horticultural characteristics to plants of the unnamed, unpatented proprietary seed parent. However, the new variety has a larger overall flower and smaller leaf size than the seed parent. Additionally, plants of 'SLSDB17-0' produce different colored flowers, with different markings, as well as shorter peduncles than the seed parent.

Plants of the new cultivar 'SLSDB17-0' are similar in most horticultural characteristics to plants of the unnamed, unpatented proprietary pollen parent. However, the new variety has a larger flower and smaller leaf size than the pollen parent. Additionally, plants of 'SLSDB17-0' produce flowers with different colored lobes and markings than the pollen parent.

COMPARISON TO COMMERCIAL VARIETY

The new cultivar can be compared to the commercial variety 'Harlequin Blue', unpatented. Plants of the two cultivars are similar in most horticultural characteristics, however, plants of 'SLSDB17-0' produce more leaves and larger leaves as well as flowering earlier. Additionally, plants of 'SLSDB17-0' produce larger flowers with different floral lobe coloring.

The new cultivar can be compared to the commercial variety 'Bethan', unpatented. Plants of the two cultivars are similar in most horticultural characteristics, however, plants of 'SLSDB17-0' produce larger flowers with different lobe coloring. Additionally, plants of 'SLSDB17-0' produce more leaves of larger size.

BRIEF DESCRIPTION OF THE PHOTOGRAPHS

The accompanying photograph in FIG. 1 illustrates in full color a typical flower of 'SLSDB17-0'.

Figure 2:
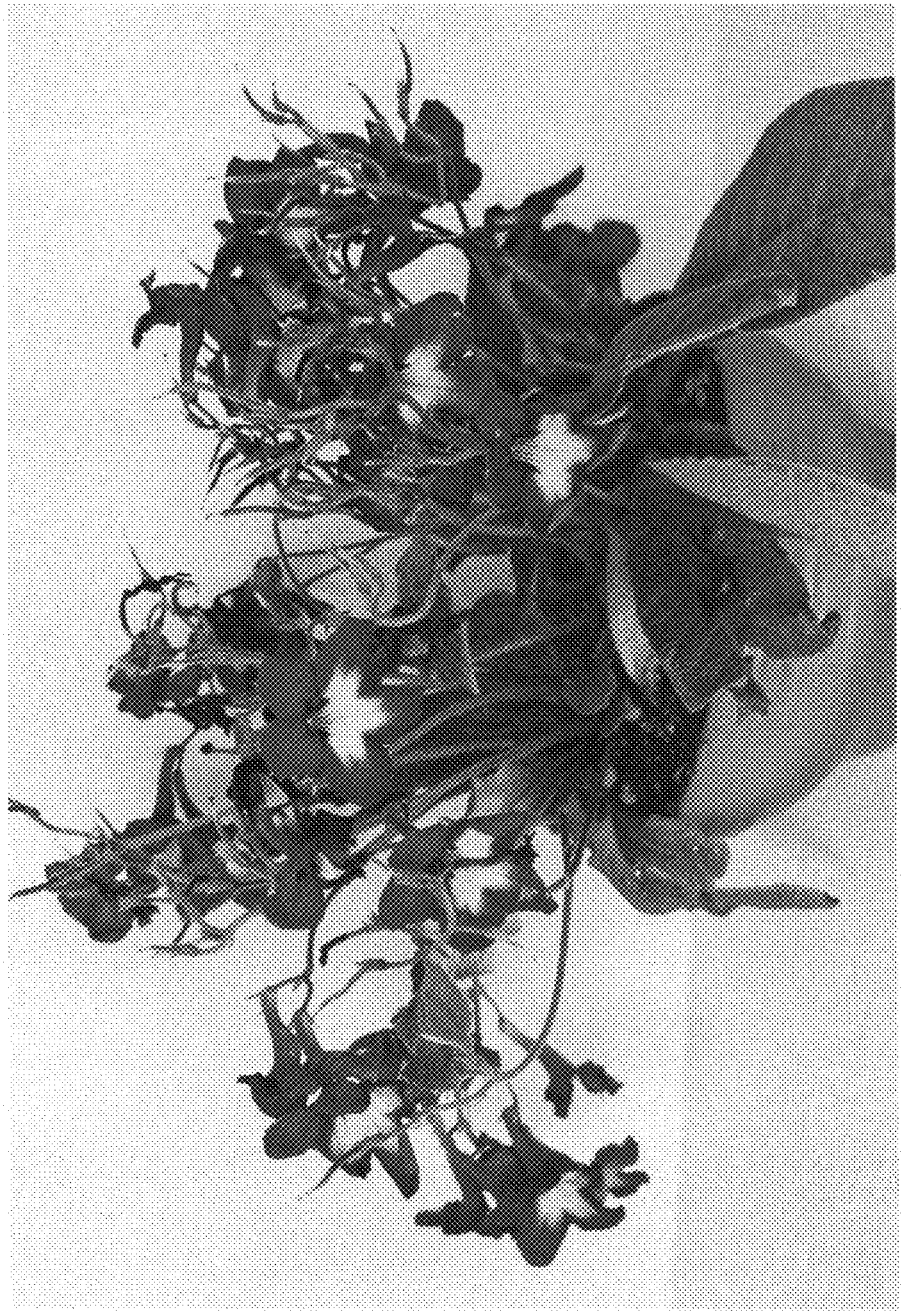

FIG. 2 illustrates a typical plant of 'SLSDB17-0' grown in a greenhouse, in an 8 inch commercial pot. Age of the plant photographed is approximately 30 weeks from a rooted cutting.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2001 except where general terms of ordinary dictionary significance are used. The following observations and measurement describe 'SLSDB17-0' plants grown in a commercial greenhouse in Oxnard, Calif. The growing temperature ranged from approximately 12° C. to 30° C. The greenhouse is subject to partial shade. General light conditions are bright, normal sunlight with some shade during the brightest part of the day. Measurements and numerical values represent averages of typical plant types.

Botanical classification: *Streptocarpus* hybrid 'SLSDB17-0'.

PROPAGATION

Time to initiate roots: About 20 to 25 days at approximately 21 to 25° C.

Root description: Fine, fibrous.

PLANT

Growth habit: Upright.

Age of the plant described: Approximately 30 weeks from a well rooted cutting.

Pot size of plant described: 8 inch pot.

Height: Approximately 13 cm from soil line to top of foliar plane. Approximately 23 cm to top of highest flower.

Plant spread: Approximately 35 cm at widest point.

Growth rate: Moderate.

Branching characteristics: Basal rosettes of foliate, no stem, no branches.

FOLIAGE

Leaf:

*Arrangement*.—Rosette.

*Quantity*.—Average 12 to 55 leaves.

*Average length*.—Approximately 17 cm.

*Average width*.—Approximately 6 cm.

*Shape of blade*.—Lanceolate.

*Apex*.—Acute.

*Base*.—Attenuate.

*Margin*.—Crenate.

*Appearance of top surface*.—Matte.

*Appearance of bottom surface*.—Matte.

*Pubescence*.—Very short, less than 1 mm hairs, densely covering top and bottom leaf surfaces.

*Aspect*.—Somewhat undulating, overall leaf reflexes downward in older foliage.

*Color*.—Young foliage upper side: Near RHS Green 137C. Young foliage under side: Near RHS Green 138B. Mature foliage upper side: Near RHS Green 137B. Mature foliage under side: Near RHS Green 138B.

*Venation*.—Type: Pinnate. Venation color upper side: Near RHS Green 143B. Venation color under side: Near RHS Yellow-Green 145B.

*Petiole*.—Not present, leaves sessile.

FLOWER

Natural flowering season: Continuous.

Inflorescence and flower type and habit: Racemes of 2 to 4 asymmetrical funnel shaped flowers.

Inflorescence longevity on plant: At least 2 weeks before any significant change is observed.

Approximate quantity of flowers per plant: Approximately 45 mature and immature flowers per plant.

Flowers: Persistent.

Inflorescence:

*Diameter of entire inflorescence*.—Approximately 13.5 cm.

*Depth of inflorescence*.—Approximately 8.0 cm.

Individual flower bud:

*Shape*.—Tubular, with spherical apex.

*Length*.—Approximately 4.0 cm.

*Diameter*.—Approximately 1.9 cm.

*Color*.—Near RHS Purple N79D, apex Purple N79A.

Flowers:

*Flower length*.—6.5 cm.

*Flower width*.—7.0 cm.

*Upper petals* (*upper lip*).—Number: 2, fused together at base. Length: 3.0 cm. Width: 2.5 cm. Shape: Obicular. Apex: Obtuse, ruffled. Margin: Shallow crenate. Texture: Velvety, all surfaces. Pubescent outersurface. Color: When opening: Inner surface: RHS Purple-Violet N81B. Outer surface: RHS Purple N78A. Fully opened: Inner surface: RHS Purple-Violet N81A, base flushed Purple N79A. Outer surface: RHS Purple N78A. Aging: Inner surface: RHS Violet 83A, base Purple N79A. Outer surface: RHS Purple 77A.

*Lower petals* (*lower lip*).—Quantity: 3. Length: 3.0 cm. Width: 2.5 cm. Shape: Orbicular, fused at base. Apex shape: Obtuse. Margin: Shallow crenate, undulating. Texture: Velvety, all surfaces. Pubescent outer surface. Color: When opening: Inner surface: RHS Purple-Violet N81A, base Yellow-White 158D and Yellow 10D. Outer surface: RHS Purple-Violet N81A. Fully opened: Inner surface: RHS Purple-Violet N81A, base Yellow-White 158D. Outer surface: RHS Purple-Violet N81A. Aging: Inner surface: RHS Violet 83A, base Yellow-White 158B. Outer surface: RHS Purple N79C.

*Throat*.—Length: 3.0 cm. Width: 1 cm, at widest point. Texture: glabrous, shiny inner surface. Outer surface pubescent. Color: When opening: Inner surface: RHS Purple-Violet N81 with stripes Yellow-White 158D and Yellow 10D. Outer surface: RHS Purple N79C. Fully opened: Inner surface: RHS Purple-Violet N81 with stripes Yellow-White 158D and Yellow 10D. Outer surface: RHS Purple N79C with stripes Purple N78C. Aging: Inner surface: RHS Purple-Violet N81 with stripes Yellow-White 158D and Yellow 10D. Outer surface: RHS Purple N79C with stripes Purple N78C.

Sepals:

*Quantity*.—Average 5.

*Shape*.—Narrow deltate, base fused.

*Length*.—Approximately 0.6 cm.

*Width*.—Approximately 0.2 cm.

*Apex*.—Acute.

*Base*.—Fused.
*Margin*.—Entire.
*Texture*.—Highly pubescent, all surfaces.
*Color*.—Upper Surface: Near RHS Green 137A. Lower Surface: Near RHS Green 137A.

Peduncle:
*Length*.—Longest average 16 cm. Shortest average 10 cm.
*Diameter*.—Approximately 0.4 cm.
*Texture*.—Densely pubescent.
*Color*.—Near RHS Yellow-Green 144B.
*Orientation*.—Approximately 90 to 75 degree angle from rosette undulating.

Pedicel:
*Length*.—Average range 0.8 cm to 1.5 cm.
*Diameter*.—Approximately 0.3 cm.
*Texture*.—Soft, dense pubescence.
*Color*.—Near RHS Yellow-Green 144B, flushed with Purple N77A.
*Orientation*.—Approximately 30 degree angle from peduncle. Straight, or slightly outwardly curved.

Fragrance: None.

REPRODUCTIVE ORGANS

Stamens:
*Number*.—2.
*Filament length*.—Approximately 0.7 cm, unfused section.

Anthers:
*Length*.—Approximately 0.2 cm.
*Shape*.—Bi-lobed.
*Color*.—Near RHS White N155C.
*Pollen*.—Not observed.

Pistil:
*Number*.—1.
*Length*.—Approximately 2.5 cm.
*Style*.—Length: Approximately 2.0 cm. Color: Near RHS Greyed-Purple N187C from base to approximately 50% of length. Upper 50% near White N155A.
*Stigma*.—Shape: Bifurcate. Color: Near RHS White N155C.

OTHER CHARACTERISTICS

Seeds and fruits: Not observed.
Disease/pest resistance: Neither resistant nor susceptible to normal diseases and pests of *Streptocarpus*.
Temperature tolerance: USDA zones 9-11.

What is claimed is:

1. A new and distinct cultivar of *Streptocarpus* plant named 'SLSDB17-0' as herein illustrated and described.

* * * * *